United States Patent
Dockner et al.

(10) Patent No.: US 6,559,340 B2
(45) Date of Patent: May 6, 2003

(54) PROCESS FOR PREPARING N-SUBSTITUTED HYDROXYLAMINES AND SALTS THEREOF

(75) Inventors: Michael Dockner, Köln (DE); Wolfgang Eymann, Köln (DE); Bernd-Michael König, Bergisch Gladbach (DE); Helmut Holzem, Köln (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/013,203

(22) Filed: Dec. 7, 2001

(65) Prior Publication Data

US 2002/0082453 A1 Jun. 27, 2002

(30) Foreign Application Priority Data

Dec. 11, 2000 (DE) .......................... 100 61 623

(51) Int. Cl.$^7$ ........................................... C07C 239/10
(52) U.S. Cl. ...................... 564/300; 564/301
(58) Field of Search ................. 564/300, 301

(56) References Cited

U.S. PATENT DOCUMENTS 5,808,150 A * 9/1998 Michelotti .................. 564/2

FOREIGN PATENT DOCUMENTS

| EP | 0 217 269 | | 8/1990 | |
| WO | 00/02848 | * | 1/2000 | .......... C07C/239/10 |

OTHER PUBLICATIONS

J. Am. Chem. Soc. 79, (month unavailable) 1957, p. 5749, "Preparation and Properties of Oxazirdanes".

J. Chem. Soc. Perkin Trans, 1, (month unavailable) 1990, pp. 301–306, Derek R. Boyd, Peter B. Coulter, M. Rosaleen McGuckin and Narain D. Sharma, "Imines and Derivatives, Part 24, Nitrone Synthesis by Imine Oxidation using either a Peroxyacid or Dimenthyldioxirane".

J. Chem. Soc. Perkin Trans, 1, (month unavailable) 1990, pp. 2385–2390, Toru Minami, Kazunari Hirakawa, Shinichiro Koyanagi, Seigo Nakamura and Masahiko Yamaguchi, "A New Synthesis of α–Methylene Lactones".

Tetrahedron Letters, No. 28, (month unavailable) 1974, pp. 2453–2456, T. Polonski and A. Chimiak, "Oxidation of Amino Acid Esters into N–Hydroxyamino Acid Derivatives".

* cited by examiner

Primary Examiner—Brian J. Davis
(74) Attorney, Agent, or Firm—Godfried R. Akorli; Richard E. L. Henderson

(57) ABSTRACT

This invention relates to a process for preparing N-substituted hydroxylamines from N-substituted aryl- or heteroaryloxaziridines by acid hydrolysis and isolation of the N-substituted hydroxylamines in the form of their salts.

16 Claims, No Drawings

PROCESS FOR PREPARING N-SUBSTITUTED HYDROXYLAMINES AND SALTS THEREOF

BACKGROUND OF THE INVENTION

The present invention relates to a process for preparing N-substituted hydroxylamines from N-substituted aryl- or heteroaryloxaziridines by acid hydrolysis and also the isolation of the N-substituted hydroxylamines in the form of their salts.

N-Substituted hydroxylamines and in particular N-alkyl-hydroxylamines and salts thereof serve as starting materials and intermediates in the synthesis of pharmaceutically active compounds.

From J. Am. Chem. Soc. 79, 5739 (1957), it is already known that N-alkyl-oxaziridines can be converted into aldehydes and N-alkyl-hydroxylamines by acid hydrolysis. What is described is in particular the hydrolysis of 2-tert-butyl-3-phenyloxaziridine in the presence of 1.13 mol of sulfuric acid in methanol. After 20 hours at room temperature, the 2-tert-butyl-3-phenyloxaziridin is hydrolyzed to benzaldehyde and N-(tert-butyl)hydroxylamine. To isolate the hydroxylamine, the reaction mixture is initially mixed with water. The benzaldehyde is then removed by extraction with diethyl ether from the sulfuric-acid-containing medium. By addition of aqueous sodium hydroxide solution, the aqueous phase is made strongly alkaline, and the N-(tert-butyl)hydroxylamine is then extracted from the aqueous phase continuously for three days, using diethyl ether. The organic phase is dried and the solvent is removed, giving N-(tert-butyl)hydroxylamine in a yield of 82%. For an industrial process, an extraction time of three days is not particularly suitable, and this time can, if at all, only be reduced by using a special apparatus. Furthermore, our own examination of this extraction process has shown that, from a strongly alkaline medium (pH≧12), only 20% of the amount of product to be expected theoretically can be extracted with methylene chloride.

From EP-A 217,269 it is known that, in addition to sulfuric acid, hydrochloric acid is also suitable for hydrolyzing oxaziridines. In this case, the reaction is complete even after a reaction time of one hour. The aromatic aldehyde formed is extracted from the acidic aqueous phase using diethyl ether. The hydrochloride of the N-substituted hydroxylamine is then obtained in good yields by concentrating the aqueous phase and drying the residue. However, thermal tests have shown that the hydrochloride begins to decompose at temperatures above 50° C. The elevated temperatures that are usually required for distilling off the water are therefore unsuitable.

If N-alkyl-substituted hydroxylamines are to be used as inter-mediates and/or biologically active compounds, it is advantageous to provide them in a storage-stable form. In general, in particular the N-alkyl-substituted hydroxylamines are unsatisfactory with respect to their storage stability. In contrast, the salts of the N-alkyl-substituted hydroxylamines generally have a considerably better storage stability, and their isolation is therefore of greater interest. If the starting material required is the free hydroxylamine, it can be released immediately prior to use from the salts by adding base.

WO-A 00/02848 describes carboxylates of N-(tert-butyl) hydroxylamine. To prepare these carboxylates, initially 2-tert-butyl-3-phenyl oxaziridine is hydrolyzed using 1.5 equivalents of sulfuric acid. However, even after a reaction time of 20 hours, GC still shows 5.8 area per cent of starting material (Example 4). Complete conversion is observed only after two more days. The benzaldehyde formed is, as in the cases cited above, removed from the crude mixture by extraction. In contrast to other processes known from the literature, the further procedure comprises (1) adding a lower carboxylic acid RCOOH, where R represents methyl, ethyl, n-propyl, isopropyl, n-butyl, isobutyl, or t-butyl, to the reaction mixture, (2) setting a pH of about 5.5 by adding aqueous sodium hydroxide solution, (3) then extracting the carboxylates of the N-(tert-butyl)hydroxylamine from the weakly acidic medium using ethyl acetate, and (4) isolating the carboxylates by crystallization from ethyl acetate or toluene or by distillation. However, in the preparation of N-(tert-butyl)hydroxylammonium acetate from 2-tert-butyl-3-phenyloxaziridine, this route gives, after distillation and subsequent crystallization, only 45% of the desired product. As shown by differential thermoanalysis of, for example, N-(tert-butyl)-hydroxylammonium acetate, the salt begins to decompose even at 70° C., with a heat production rate of 1 W/kg. The ethyl acetate should therefore be removed under reduced pressure. Additional thermal stress for distilling the N-(tert-butyl)hydroxylammonium acetate to purity is therefore not to be recommended.

All known methods for preparing N-substituted hydroxylamines and in particular N-alkyl-hydroxylamines and salts thereof by acid hydrolysis of aryloxaziridines in aqueous medium are unsatisfactory for implementation on an industrial scale, with respect to reaction time, isolation method, extraction times, and the solvents used. There is therefore a need for an economical and safe process for producing N-substituted hydroxylamines and salts thereof.

SUMMARY OF THE INVENTION

The present invention provides a process for preparing N-substituted hydroxylamines of the general formula (I) and salts thereof

where

R may represent
 (i) a radical of the general formula (II)

in which
  $R^1$, $R^2$, and $R^3$ independently of one another represent hydrogen, straight-chain or branched $C_1$–$C_{20}$-alkyl, $C_3$–$C_8$-cycloalkyl, straight-chain or branched $C_2$–$C_{10}$-alkenyl or $C_6$–$C_{10}$-aryl, or
 (ii) a $C_3$–$C_8$-cycloalkyl radical, comprising
(1) acidically hydrolyzing aryl- or heteroaryloxaziridines of the general formula (III)

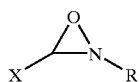

(III)

in which
R has the meaning given above for formula (I), and
X represents a $C_6$–$C_{12}$-aryl radical or a $C_3$- or $C_5$-heteroaryl radical, using at least two equivalents of an acid and a water-miscible solvent, and (2) isolating the N-substituted hydroxylamines in the form of their salts of the general formula (IV)

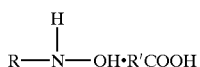

(IV)

where R has the meaning given above and R' represents hydrogen or $C_1$–$C_3$-alkyl, by subjecting the resulting hydrolyzed reaction mixture to the following steps:
(a) removal of the aromatic or heteroaromatic aldehyde of the formula XCHO that is also formed during the acid hydrolysis,
(b) adjustment of the reaction mixture to a pH in the range of 7 to 11,
(c) removal of the N-substituted hydroxylamine of the general formula (I) from the reaction mixture,
(d) addition of an acid R'COOH to the N-substituted hydroxylamine, and
(e) isolation of the salt of the general formula (IV).

DETAILED DESCRIPTION OF THE INVENTION

In the process according to the invention, the aryl- or heteroaryl-oxaziridines of the general formula (III) are initially cleaved hydrolytically.

Preferred acids for the acid hydrolysis are strong acids, particularly hydrochloric acid, phosphoric acid, sulfuric acid, and trifluoroacetic acid. Sulfuric acid has been found to be especially useful.

Suitable water-miscible solvents are all water-miscible organic solvents that are inert under the reaction conditions, for example, mono- and polyhydric alcohols having up to 6 carbon atoms. Preference is given to using methanol or ethanol.

If the radicals $R^1$, $R^2$, and/or $R^3$ in the radical R are alkyl radicals, these can in turn be substituted by saturated cycloalkyl radicals, aryl radicals, alkinyl radicals, and/or radicals that contain heteroatoms, such as halogen, oxygen, sulfur, nitrogen, and/or phosphorus atoms. Such saturated cycloalkyl radicals can, for example, contain 3 to 12 carbon atoms, such aryl radicals can, for example, contain 6 to 10 carbon atoms, and such alkinyl radicals can, for example, contain 2 to 6 carbon atoms. Suitable heteroatom-containing radicals are, for example, fluoro, chloro, bromo, iodo, hydroxyl, $C_1$–$C_6$-alkoxy, $C_6$–$C_{10}$-phenoxy, carboxyl, $C_1$–$C_6$-alkoxycarbonyl, nitro, amide, nitrile, mercapto, sulfonyl, phosphite, and phosphate groups.

If the radical R is a cycloalkyl radical or the radicals $R^1$, $R^2$, and/or $R^3$ in the radical R are cycloalkyl, aryl or alkenyl radicals, these can be substituted, for example, by $C_1$–$C_6$-alkyl, fluoro, chloro, bromo, hydroxyl, $C_1$–$C_6$-alkoxy, carboxyl, $C_1$–$C_6$-alkoxycarbonyl, nitro, sulfonyl, and/or nitrile groups.

Particularly suitable are aryl- or heteroaryloxaziridines of the formula (III) in which R represents
(i) a radical of the general formula (II)

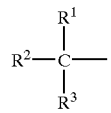

(II)

in which
$R^1$, $R^2$, and $R^3$ independently of one another represent hydrogen, straight-chain or branched $C_1$–$C_{10}$-alkyl, $C_3$–$C_6$-cycloalkyl, straight-chain or branched $C_2$–$C_6$-alkenyl, or phenyl, or
(ii) a $C_3$–$C_6$-cycloalkyl radical.

The radicals $R^1$, $R^2$, and $R^3$ independently of one another particularly preferably represent hydrogen, methyl, ethyl, propyl, isopropyl, butyl, isobutyl, pentyl, isopentyl, and cyclopropyl. However, nonadecyl has also been found to be suitable.

R preferably represents n-propyl, n-butyl, isobutyl, t-butyl, n-pentyl, cyclopropyl, cyclopentyl, or cyclohexyl.

Particularly suitable also are aryl- or heteroaryloxaziridines of the formula (III) in which X may represent phenyl, naphthyl, or a radical of the formulas (Va) or (Vb)

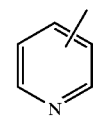

(Va)

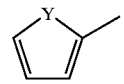

(Vb)

wherein Y represents N, O, or S and the bond to the oxaziridine ring may be located in a position ortho, meta, or para to the nitrogen of the pyridine ring (Va).

If X represents a phenyl or naphthyl radical, these can be substituted, for example, by $C_1$–$C_6$-alkyl, fluoro, chloro, bromo, hydroxyl, $C_1$–$C_6$-alkoxy, $C_1$–$C_6$-alkoxycarbonyl, nitro, sulfonyl, and/or nitrile groups. X represents in particular a 4-methoxyphenyl, 4-methylphenyl or 4-nitro phenyl radical.

In the process according to the invention, it is preferably possible to cleave 2-tert-butyl-3-phenyloxaziridine into N-(tert-butyl)hydroxylamine and benzaldehyde, to cleave 2-isopropyl-3-(4-nitrophenyl)oxaziridine and 2-isopropyl-3-(4-methoxyphenyl)oxaziridine into N-(isopropyl)hydroxylamine and 4-nitrobenzaldehyde and 4-methoxybenzaldehyde, respectively, to cleave 2-cyclohexyl-3-(4-methylphenyl)-oxaziridine into N-(cyclohexyl)hydroxylamine and 4-methylbenzaldehyde, to cleave 2-cyclopropyl-3-phenyloxaziridine into N-(cyclopropyl)hydroxylamine and benzaldehyde, and to cleave 2-cyclopropylmethyl-3-phenyloxaziridine into N-(cyclopropylmethyl)hydroxylamine and benzaldehyde.

The aryl- or heteroaryloxaziridines used in the process according to the invention can be obtained by various synthesis routes. J. Am. Chem. Soc. 79, 5749 (1957), for example, describes that arylaldimines that contain an unsubstituted phenyl group or a phenyl group substituted by a nitro group can be converted with anhydrous peracetic acid into the corresponding oxaziridine, which can be isolated by distillation. From EP-B 217,269, it is furthermore known that N-alkyl-substituted aryloxaziridines can be obtained by reacting arylaldimines with perpropionic acid in benzene. m-Chloroperbenzoic acid, too, can be used for oxidizing aryl aldimines (J. Chem. Soc. Perkin Trans 1 1990, 301 and 2390). Also known is the oxidation of benzylideneamino acid esters to the corresponding oxaziridines using monoperphthalic acid in the solvent diethyl ether (Tetrahedron Lett. 28, 2453 (1974)).

The process according to the invention is usually carried out by initially preparing a mixture of the N-aryl- or heteroaryloxaziridine and the water-miscible solvent. The concentration of the N-substituted aryl- or heteroaryloxaziridine in the solvent can be varied within wide ranges and can be, for example, from 5 to 80% by weight, preferably from 20 to 50% by weight, particularly from 35 to 40% by weight.

A solution of the acid in water is added to the resulting mixture. The rate at which the solution is metered in is expediently chosen such that, in spite of the heat of reaction that has to be dissipated, the reaction temperature does not exceed 25° C. The lower limit for the reaction temperature can, for example, be 0° C. Preference is given to reaction temperatures in the range from 10 to 25° C.

Based on 1 mol of N-substituted aryl- or heteroaryloxaziridine, at least 2 equivalents of acid have to be used. Preference is given to using from 2.0 to 5.0 equivalents of acid, particularly preferably from 2.0 to 2.5 equivalents of acid, particularly from 2.1 to 2.5 equivalents of acid. The concentration of the acid in water can be varied within wide ranges and can, for example, be from 10 to 52% by weight. 35–37% strength hydrochloric acid and 48 to 52% strength sulfuric acid, for example, have been found to be suitable.

After the addition of acid has ended, the reaction mixture can be stirred at, for example, from 5 to 30° C. (preferably from 15 to 25° C.) until the end of the reaction is established, for example, by gas chromatography. In general, even after very short reaction times of three to four hours, no more starting material is found in the GC chromatogram.

In addition to the formation of the desired N-substituted hydroxylamine, an aromatic or heteroaromatic aldehyde of the formula XCHO is formed during the hydrolysis. For the hydrolytic cleavage of 2-tert-butyl-3-phenyloxaziridine, this aldehyde is benzaldehyde.

After the acid hydrolysis has been carried out, this aromatic or heteroaromatic aldehyde is removed from the reaction mixture (step (a)). This removal is expediently carried out by extraction. However, distillation is also possible. The extraction is usually carried out at room temperature. Methylene chloride has been found to be a particularly suitable extracting agent. In the case of the prior acid hydrolysis of N-substituted phenyloxaziridines, more than 95% of the theoretical amount of the benzaldehyde can be removed from the aqueous phase by two to three extractions using in each case one equivalent by volume of methylene chloride. In addition to the benzaldehyde, it is also possible for minute amounts of the dimethyl acetal of the benzaldehyde to be formed during the hydrolysis. This compound is also removed in the extraction.

In step (b), the reaction mixture is adjusted to a pH in the range from 7 to 11. This is usually carried out by adding a water-soluble base. The reaction mixture is preferably adjusted to a pH of 8 to 10, particularly preferably 8.5 to 9.5.

Suitable water-soluble bases are, in principle, ammonia, water-soluble primary, secondary, and tertiary amines and alkali metal and alkali earth metal oxides, hydroxides, carbonates, bicarbonates, hydrogen phosphates, and phosphates. Preference is given to using sodium hydroxide or potassium hydroxide.

The water-soluble base is added to the reaction mixture at, for example, from 0 to 30° C., preferably at from 10 to 25° C. The concentration of the base can be varied as desired and can, for example, be from 10 to 50% by weight. Preference is given to 25 to 45% by weight strength solutions. A 28% by weight strength solution of ammonia, for example, has been found to be suitable. Primary, secondary, and tertiary amines can also be used as such, i.e., without water.

During the addition of the base, such as, for example, an alkali metal or alkaline earth metal oxide, hydroxide, carbonate, bicarbonate, hydrogen phosphate or phosphate, a solid may form but can easily be filtered off. If the acid used for the acid hydrolysis is sulfuric acid, the addition of aqueous sodium hydroxide solution results in the precipitation of sodium sulfate that is removed by filtration.

In step (c), the N-substituted hydroxylamine is removed from the reaction mixture. This can take place in the form of two alternatives (c1) or (c2).

In alternative (c1), initially an organic solvent is added to the reaction mixture, which results in the N-substituted hydroxylamine passing into the organic solvent phase, and the organic solvent phase that contains the N-substituted hydroxylamine is then separated off.

Suitable organic solvents are low-boiling, polar, water-miscible organic solvents. Suitable are, for example, branched and unbranched alkyl ethers, such as tert-butyl methyl ether (b.p. 55–56° C.), and also halogenated saturated hydrocarbons, such as methylene chloride (b.p. 39.8–40° C.) and 1,2-dichloroethane (b.p. 83° C.). Preference is given to using methylene chloride. The organic solvent phase is then separated off, usually by extraction. In the case of the preparation of N-(tert-butyl)hydroxylamine from 2-tert-butyl-3-phenyloxaziridine, the extraction process has to be carried out repeatedly, due to the solubility in water of the N-(tert-butyl)hydroxylamine. If 2.7 parts by weight of methylene chloride are used, based on the 2-tert-butyl-3-phenyloxaziridine used, five extractions are sufficient. In this way, 70 to 80% of the N-(tert-butyl)hydroxylamine are transferred into the organic phase.

In alternative (c2), the N-substituted hydroxylamine is removed from the reaction mixture by distillation.

In step (d), an acid R'COOH is added to the N-substituted hydroxylamine, where R' represents hydrogen or $C_1$–$C_3$-alkyl. R' preferably represents methyl, ethyl, n-propyl, n-butyl, isobutyl, or tert-butyl. R' represents particularly methyl (i.e., when acetic acid is used).

If, prior to step (d), alternative (c1) has been carried out, the N-substituted hydroxylamine is present in an organic solvent. When using alternative (c2), however, the N-substituted hydroxylamine is present as such.

By adding the acid, the desired salt of the general formula (IV) is formed. It is expedient to determine the content of N-(tert-butyl)hydroxylamine in the combined organic phases beforehand, by titration against hydrochloric acid. Depending on the desired salt of the N-substituted hydroxylamine, from 0.9 to 1.2 equivalents of the corresponding acid R'COOH, based on the content of N-substituted hydroxylamine in the combined organic phases, are added. The amount of acid used is preferably from 0.95 to 1.05 equivalents.

In step (e), the salt of the N-substituted hydroxylamine of the general formula (IV) is isolated.

To this end, the reaction mixture is, after the addition of acid, usually initially concentrated to a volume in which the salt is only just soluble. In general, from 80 to 95% of the original volume (preferably from 90 to 93%) are distilled off to this end. Due to the thermal instability of the salts of the N-(tert-butyl)hydroxylamine, the jacket temperature of the reactor must not exceed 50° C. during the distillation. If the solvent used does not boil at the maximum jacket temperature, the operation has to be carried out under an appropriately reduced pressure.

The subsequent isolation is preferably carried out by crystallization from a mixture of methylene chloride and cyclohexane.

To precipitate the salt, the concentrate can be added, at from 10 to 30° C., to cyclohexane. The salt is preferably precipitated at from 20 to 25° C. To bring the formation of precipitate to completion, the mixture may be cooled to from 8 to 12° C. The precipitate is filtered off, washed with cyclohexane, and then dried under slightly reduced pressure at from 15 to 30° C., particularly from 20 to 25° C. The preferred embodiment comprises blowing a weak stream of nitrogen over the salt, at from 20 to 25° C. and 800±20 mbar.

Work-up of the reaction mixture via steps (a) to (e) gives the salt of the N-substituted hydroxylamine of the general formula (IV) in a yield of about 70% of theory. A possible impurity may be very low amounts of the N-substituted aryl- or heteroarylnitrone, which is formed from residual amounts of benzaldehyde and N-substituted hydroxylamine when the solvent is distilled off. In the case of the preparation of N-(tert-butyl)hydroxylamine, this nitrone is tert-butyl-phenylnitrone.

The process according to the invention can be carried out in a simple manner; if steps (a) to (e) are followed, there are no problems with regard to safety, the N-substituted hydroxylamine can, in the stated pH range, be extracted from the aqueous phase in an efficient manner, the yields that can be obtained are very good, and upscaling problems can be solved without special expenditure. Furthermore, the reaction times of the process are short. Usually, even after at most 4 hours, complete acid hydrolysis has occurred.

The following examples further illustrate details for the process of this invention. The invention, which is set forth in the foregoing disclosure, is not to be limited either in spirit or scope by these examples. Those skilled in the art will readily understand that known variations of the conditions of the following procedures can be used. Unless otherwise noted, all temperatures are degrees Celsius and all percentages are percentages by weight.

EXAMPLES

Example 1

At room temperature, 93.9 g of 2-tert-butyl-3-phenyloxaziridine and 148.0 g of methanol were initially charged in a 1 liter double-jacketed plane-joint beaker with bottom outlet, glass stirrer, temperature sensor, dropping funnel, and condenser. Over a period of 30 minutes, 196.1 g of a 50% strength sulfuric acid were added dropwise to this solution, without exceeding an internal temperature of 25° C. The reaction mixture was stirred at from 20 to 25° C. for four hours. At the same temperature, the sulfuric acid-containing solution was then extracted three times with in each case 132 g of methylene chloride. By carrying out this extraction, more than 95% of the benzaldehyde formed could be recovered. At a maximum internal temperature of 30° C., the pH of the sulfuric acid-containing aqueous phase was adjusted to pH 9 by addition of 45% strength aqueous sodium hydroxide solution. The resulting precipitate was filtered off and washed once with 251 g of methylene chloride. The aqueous phase was extracted once with the methylene chloride used for washing the sodium sulfate that had been filtered off and four more times with in each case 251 g of methylene chloride. The content of N-(tert-butyl) hydroxylamine in the combined organic phases was determined by titration of a 2 g sample against 1 M hydrochloric acid. At from 20 to 25° C., the combined organic phases were treated with 1.0 equivalents of acetic acid. At a maximum jacket temperature of 50° C., such an amount of methylene chloride was distilled off that about 10% of the original volume remain in the 1 liter double-jacketed plane-joint beaker. With vigorous stirring, the yellowish concentrate was added, at room temperature, to 160 g of cyclohexane that had earlier been admixed with a few seed crystals. After the addition had ended, the suspension was cooled to 10° C., and the product was filtered off at from 8 to 12° C. The pale-yellow solid was washed once with 78 g of cold cyclohexane and then dried in a stream of nitrogen at from 20 to 25° C. and 800 mbar. This gave 53 g of a pale-yellow solid. This corresponds to a yield of 70% of theory of N-(tert-butyl)hydroxylammonium acetate. Gas-chromatographic analysis of the isolated product showed:

| N-(tert-butyl)hydroxylamine: | 99.7 area % |
|---|---|
| N-tert-butyl-phenylnitrone: | 0.3 area % |

What is claimed is:

1. A process for preparing N-substituted hydroxylamines of the formula (I) and salts thereof,

where R represents
(i) a radical of the formula (II)

in which
R$^1$, R$^2$, and R$^3$ independently of one another represent hydrogen, straight-chain or branched C$_1$–C$_{20}$-alkyl, C$_3$–C$_8$-cycloalkyl, straight-chain or branched C$_2$–C$_{10}$-alkenyl or C$_6$–C$_{10}$-aryl, or
(ii) a C$_3$–C$_8$-cycloalkyl radical, comprising
(1) acidically hydrolyzing aryl- or heteroaryloxaziridines of the formula

in which
R has the meaning given above for formula (I), and
X represents a C$_6$–C$_{12}$-aryl radical or a C$_4$ or C$_5$-heteroaryl radical, using at least two equivalents of an acid and a water-miscible solvent, and
(2) isolating the N-substituted hydroxylamines in the form of their salts of the formula (IV)

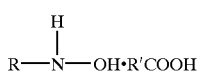

(IV)

where R has the meaning given above and R' represents hydrogen or $C_1$–$C_3$-alkyl, by subjecting the resulting hydrolyzed reaction mixture to the following steps:

(a) removal of the aromatic or heteroaromatic aldehyde of the formula XCHO that is also formed during the acid hydrolysis, (b) adjustment of the reaction mixture to a pH in the range of 7 to 11, (c) removal of the N-substituted hydroxylamine of the formula (I) from the reaction mixture, (d) addition of an acid R'COOH to the N-substituted hydroxylamine, and (e) isolation of the salt of the formula (IV).

2. A process according to claim 1 wherein the acid used for hydrolysis is hydrochloric acid, phosphoric acid, sulfuric acid, or trifluoroacetic acid.

3. A process according to claim 1 wherein the water-miscible solvent used for hydrolysis is a mono- or polyhydric alcohol having up to 6 carbon atoms.

4. A process according to claim 1 wherein R in the aryl- or heteroaryloxaziridines of the formula (III) represents (i) a radical of the formula (II)

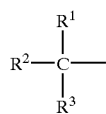

(II)

in which $R^1$, $R^2$, and $R^3$ independently of one another represent hydrogen, straight-chain or branched $C_1$–$C_{10}$-alkyl, $C_3$–$C_6$-cycloalkyl, straight-chain or branched $C_2$–$C_6$-alkenyl, or phenyl, or (ii) a $C_3$–$C_6$-cycloalkyl radical.

5. A process according to claim 1 wherein the radicals $R^1$, $R^2$, and $R^3$ in formula (II) independently of one another represent hydrogen, methyl, ethyl, propyl, isopropyl, butyl, isobutyl, pentyl, isopentyl, or cyclopropyl.

6. A process according to claim 1 wherein the radical R represents n-propyl, n-butyl, isobutyl, t-butyl, n-pentyl, cyclopropyl, cyclopentyl, or cyclohexyl.

7. A process according to claim 1 wherein X in the aryl- or heteroaryloxaziridines of the formula (III) represents phenyl, naphthyl, or a radical of the formula (Va) or (Vb)

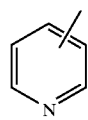

(Va)

(Vb)

wherein Y represents N, O, or S and the bond to the oxaziridine ring is located in a position ortho, meta, or para to the nitrogen of the pyridine ring (Va).

8. A process according to claim 1 wherein 2-tert-butyl-3-phenyloxaziridine is cleaved into N-(tert-butyl) hydroxylamine and benzaldehyde; 2-isopropyl-3-(4-nitrophenyl)oxaziridine and 2-isopropyl-3-(4-methoxyphenyl)oxaziridine are cleaved into N-(isopropyl) hydroxylamine and 4-nitrobenzaldehyde and 4-methoxybenzaldehyde, respectively; 2-cyclohexyl-3-(4-methylphenyl)-oxaziridine is cleaved into N-(cyclohexyl) hydroxylamine and 4-methylbenzaldehyde; 2-cyclopropyl-3-phenyloxaziridine is cleaved into N-(cyclopropyl) hydroxylarnine and benzaldehyde; or 2-cyclopropylmethyl-3-phenyloxaziridine is cleaved into N-(cyclopropylmethyl) hydroxylamine and benzaldehyde.

9. A process according to claim 1 wherein from 2.0 to 5.0 equivalents of acid, based on 1 mol of N-substituted aryl- or heteroaryloxaziridine, are used.

10. A process according to claim 1 wherein in isolation step (b) the reaction mixture is adjusted by addition of a water-soluble base to a pH in the range of 8 to 10.

11. A process according to claim 10 wherein the water-soluble base is ammonia, a water-soluble primary, secondary, or tertiary amine, or an alkali metal and alkaline earth metal oxide, hydroxide, carbonate, bicarbonate, hydrogen phosphate, or phosphate.

12. A process according to claim 1 wherein isolation step (c) is carried out by adding an organic solvent to the reaction mixture to transfer the N-substituted hydroxylamine into the organic solvent phase and then separating off the resultant organic solvent phase that contains the N-substituted hydroxylamine.

13. A process according to claim 12 wherein the organic solvent is a low-boiling, polar, water-immiscible organic solvent.

14. A process according to claim 1 wherein in the acid R'COOH added to the organic solvent phase in step (d), R' represents methyl, ethyl, n-propyl, n-butyl, isobutyl, or tert butyl.

15. A process according to claim 1 wherein from 0.9 to 1.2 equivalents of the acid R'COOH are added in step (d), based on the amount of N-substituted hydroxylamine in the reaction mixture.

16. A process according to claim 1 wherein in step (e) the salt of the N-substituted hydroxylamine of the formula (IV) is isolated by crystallization from a mixture of methylene chloride and cyclohexane.

* * * * *